United States Patent

Viazis

Patent Number: 5,176,514
Date of Patent: Jan. 5, 1993

[54] ORTHODONTIC APPLIANCE FOR PREVENTING THUMBSUCKING

[76] Inventor: Anthony D. Viazis, 8820 Southwestern Blvd., #1221, Dallas, Tex. 75206

[21] Appl. No.: 725,015

[22] Filed: Jul. 3, 1991

[51] Int. Cl.⁵ .......................... F27D 5/00; A61F 5/37
[52] U.S. Cl. .................................. 433/2; 433/6; 128/880
[58] Field of Search ............ 433/2, 6; 128/860, 861, 128/880

[56] References Cited

U.S. PATENT DOCUMENTS

| | | | |
|---|---|---|---|
| 2,037,079 | 4/1936 | Locke | 128/136 |
| 2,077,245 | 4/1937 | Locke | 128/136 |
| 2,633,126 | 3/1953 | Newmark | 128/133 |
| 2,684,065 | 7/1954 | Umbenhower | 128/133 |
| 2,767,709 | 10/1956 | Holland | 128/133 |
| 3,522,805 | 8/1970 | Wallshein | 128/136 |
| 4,179,815 | 12/1979 | Hoffman | 433/140 |
| 4,305,709 | 12/1981 | Bruhn et al. | 433/136 |
| 4,480,994 | 11/1984 | Hoffman | 433/6 |
| 4,665,907 | 5/1987 | Leverette | 128/133 |
| 4,690,640 | 9/1987 | Hinz | 433/6 |
| 4,976,275 | 12/1990 | Dixon | 128/860 |

FOREIGN PATENT DOCUMENTS

| | | | |
|---|---|---|---|
| 1496790 | 7/1989 | U.S.S.R. | 433/2 |

OTHER PUBLICATIONS

Graber Orthodontics Principles and Practice, W. B. Saunders Co., p. 565 (1961).

Primary Examiner—Gene Mancene
Assistant Examiner—Cindy A. Cherichetti
Attorney, Agent, or Firm—Kenyon & Kenyon

[57] ABSTRACT

An orthodontic appliance corrects a habit of inserting a habit instrument, such as a thumb, within a mouth. A wire frame of the appliance has two distal ends which are doubled over and each received within a respective lingual sheath carried on a maxillary molar. Two first portions of the wire member extend anteriorly from each distal end, and each has a U-shaped loop for adjusting the position of the appliance within the mouth. Two second portions each extend anteriorly from a respective first portion, and curve downwardly through a gap formed by an overjet condition between the upper and lower incisors. A guard portion is coupled to the two curved portions and has two circular loops formed within the wire member. The two circular loops are located anteriorly with respect to the lower incisors and posteriorly with respect to the labial vestibule when the mouth is closed, and deter the insertion of a thumb (or other habit instrument) upon opening and subsequent closure of the mouth.

23 Claims, 2 Drawing Sheets

ORTHODONTIC APPLIANCE FOR PREVENTING THUMBSUCKING

FIELD OF THE INVENTION

The present invention relates to orthodontic appliances and, more particularly, to orthodontic appliances for preventing thumbsucking or the insertion of other habit instruments in the mouth.

BACKGROUND INFORMATION

Thumbsucking or the insertion of other habit instruments (e.g., other fingers) within the mouth typically causes an "overjet" condition, wherein the lower central incisors are moved both labially (out) and gingivally (down), and the upper central incisors are moved both gingivally (up) and labially (out), thus typically developing a gap between the lower and upper incisors when the mouth is closed. Although there are orthodontic treatments available for correcting overjet, the continuation of the habit during the treatment process further complicates the treatment and typically prevents successful correction of the overjet condition.

One method for correcting thumbsucking (or the insertion of other habit instruments) is to place a cage or guard device on the thumb (or other habit instrument), or to apply a foul or sharp tasting substance to the thumb or to the guard device attached to the thumb. These methods interfere with the normal use of the patient's hands, however, and thus typically do not achieve sufficient patient compliance.

Another habit correction method is to place a bar or guard device within the oral cavity of the mouth on the lingual side of the dentition to deter the insertion of the thumb (or other habit instrument) within the mouth. One such device is custom fabricated for each patient and is permanently attached on its distal ends, e.g., by soldering, to a pair of molar bands attached to the patient's upper molars. A base defines a surface which conforms to the morphology of the palate of the mouth and a guard projects downwardly from the base on the lingual side of the upper incisors. The guard is located lingually with respect to the upper incisors and typically includes several pointed surfaces to deter insertion of the thumb (or other habit instrument).

Because the guard is located lingually with respect to the dentition, the morphology of the mouth prevents the guard from having sufficient height to prevent insertion of the thumb (or other habit instrument) into the mouth. Thus, although the device hinders continuation of the habit, the device can be bypassed. The pointed surfaces on the guard can also cut the thumb tissue of particularly persistent patients. Because this device is permanently attached to molar bands (usually by soldering), once the device is no longer needed, the molar bands must be removed to discard the device, which can be a relatively time consuming procedure. This, coupled with the custom fabrication, makes the device relatively expensive.

SUMMARY OF THE INVENTION

The present invention is directed to an orthodontic appliance for correcting a habit of inserting a habit instrument within a mouth. The orthodontic appliance comprises a frame member including distal ends for being coupled to appliances supported on maxillary molars, and two first portions which each extend anteriorly from a respective distal end. A guard portion is coupled to the two first portions and is located anteriorly with respect to the lower incisors and posteriorly with respect to the labial vestibule when the mouth is closed. Upon opening of the mouth, the appliance is carried upwardly with the maxillary arch and the guard portion is located at least partially within the opening between the upper and the lower incisors to deter insertion of a habit instrument within the mouth.

One orthodontic appliance of the present invention further comprises means for adjusting the position of the frame member and the guard portion. Preferably, the frame member is made of wire and the means for adjusting includes a bendable portion located within each respective first portion for bending the respective first portion to correspondingly adjust the position of the frame member and the guard portion. Each bendable portion may define, for example, a substantially U-shaped portion of the respective first portion of the wire frame member.

One appliance of the present invention further comprises a pair of lingual sheaths, which are each carried on a respective maxillary molar for receiving a respective distal end of the frame member. Each lingual sheath preferably defines an opening for receiving a distal end of the frame member which is mesially offset relative to a tooth-abutting surface of the lingual sheath to facilitate removal and insertion of the distal end of the frame member.

In one appliance of the present invention, the frame member is made of wire and the guard portion is formed by two loops of the wire spaced apart from each other and coupled by a substantially straight portion of the wire. The appliance further comprises two second portions, each extending anteriorly from a respective first portion between the respective first portion and the guard portion, wherein each second portion is curved to extend between a gap formed between the upper and lower incisors upon closure of the mouth. Preferably, the first portions, second portions, and the guard portion are located to substantially avoid contact with the teeth and the gum tissue upon closure of the mouth.

One advantage of the appliance of the present invention, is that it substantially avoids contact with the tissue or teeth in the patient's mouth, thus providing a greater degree of patient comfort than prior habit correcting appliances. Another advantage of the appliance of the present invention, is that while the guard portion effectively prevents insertion of a thumb (or other habit instrument), the guard portion does not cut or otherwise injure the finger tissue of the patient upon attempting to insert a finger in the mouth.

Yet another advantage of the appliance of the present invention is that it permits the patient to receive food or otherwise permits the insertion of objects or instruments into the mouth when fully opened, yet prevents the patient from sucking the thumb (or other habit instrument) upon closing the mouth. Although when the mouth is fully opened the patient can receive a thumb (or other habit instrument), the mouth cannot be closed to suck the thumb, because the guard portion engages the thumb, and thus prevents the mouth from closing until the thumb is removed.

Yet another advantage of the appliance of the present invention is that the bendable portions can be adjusted by pliers, for example, to adjust the position of the frame member and the guard portion to avoid contacting the teeth and gum tissue within the patient's mouth.

Yet another advantage of the appliance of the present invention is that it can be removed from the mouth by simply removing the distal ends from the lingual sheaths and, if necessary, the appliance can be inserted again by simply inserting the distal ends back into the lingual sheaths. Thus, the appliance of the present invention is particularly advantageous in comparison to prior art devices which were soldered to molar bands.

Other advantages of the appliance of the present invention will become apparent in view of the following detailed description and drawings.

DETAILED DESCRIPTION

Figure 1:
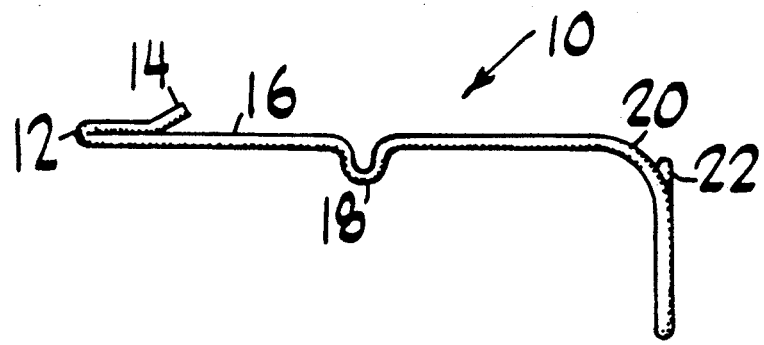
FIG. 1 is an enlarged, side plan view of an orthodontic appliance embodying the present invention.
Figure 2:
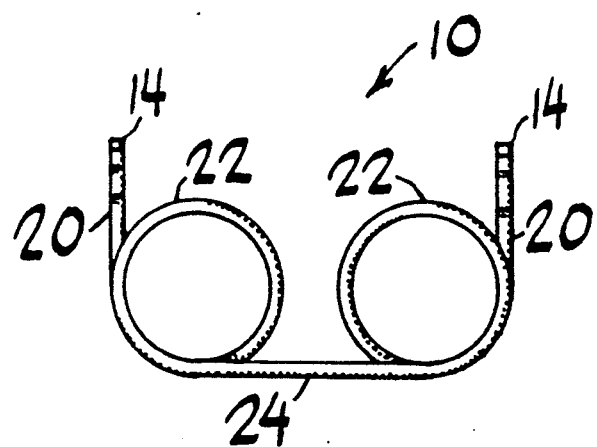
FIG. 2 is a front plan view of the orthodontic appliance of FIG. 1.
Figure 3:
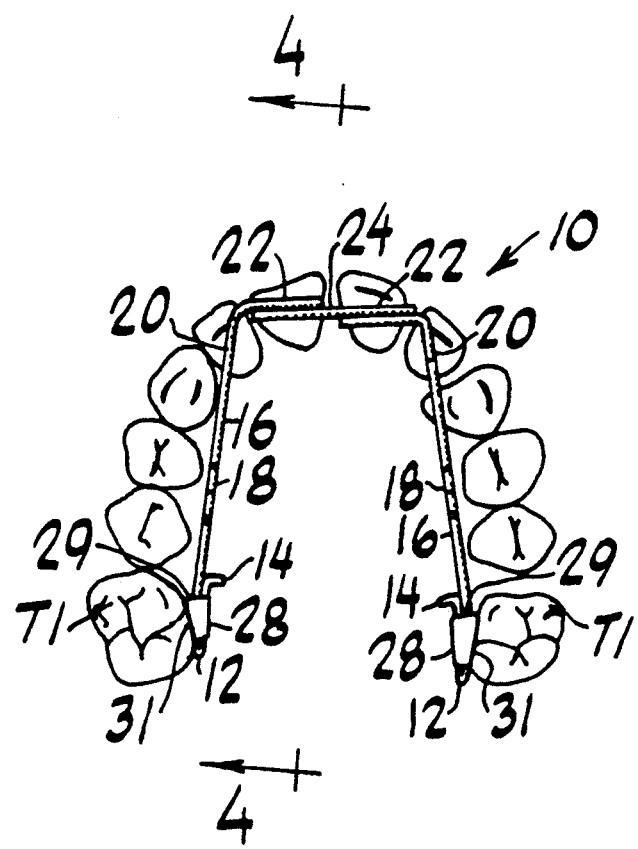
FIG. 3 is a top plan view of the orthodontic appliance of FIG. 1, shown mounted to the first molars of a typical patient's maxillary arch.

In FIG. 1, an orthodontic appliance embodying the present invention is indicated generally by the reference numeral 10. The orthodontic appliance 10 is formed from a stainless steel wire having a diameter preferably within the range of approximately 0.036 to 0.040 inches. This type of material and these dimensions are only exemplary, however, and as will be recognized by those skilled in the art, can be changed as desired. Each distal end 12 of the appliance 10 is doubled over and bent at a slight angle with respect to the doubled-over portion into an arm portion 14, as shown in FIG. 1. The arm portions 14 are provided for gripping with pliers, for example, for facilitating insertion or removal of the distal ends 12 into or from a molar appliance, as is described further below.

Two first portions 16 are formed on either side of the appliance 10, and two U-shaped loops 18 are each formed approximately in the central area of a respective first portion 16. The appliance 10 further includes two second portions 20, each located anteriorly with respect to a respective first portion 16, which both curve downwardly, as shown in FIG. 1. Two circular loops 22 are each located anteriorly with respect to a respective second portion 22, and are coupled together by a substantially straight portion 24. As will be recognized by those skilled in the art, the two circular loops 22 can be replaced with more than two such loops, a single larger loop, or another type of blocking member to deter insertion of the thumb (or other habit instrument) within the mouth, as is described further below.

Figure 4:
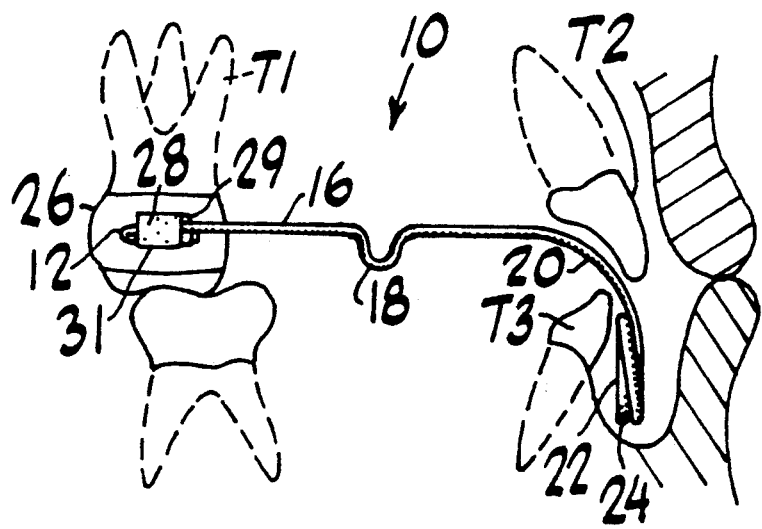
FIG. 4 is a partial view taken along the line 4—4 of FIG. 3, further illustrating the position of the appliance relative to the first molars and central incisors and relative to the labial vestibule and lips.

In the operation of the appliance 10, a pair of molar bands 26 are each attached preferably to a respective upper first molar T1, as shown in FIG. 4. A pair of lingual sheaths 28 are each coupled to a respective molar band 26. The lingual sheaths 28 are preferably a type known to those skilled in the art, such as those shown and described in U.S. Pat. Nos. 4,741,696 and 4,886,451 to Cetlin, which are each hereby expressly incorporated by reference as part of the present disclosure. As shown in FIG. 4, the two distal ends 12 of the appliance 10 are each inserted within a respective lingual sheath 28 until the doubled-over portions are received within appliance receiving passageways 29 of the lingual sheaths. Each appliance receiving passageway 29 is preferably mesially offset with respect to a tooth-abutting surface 31 of the respective lingual sheath by an acute angle to facilitate removal and insertion of the distal ends 12. In the embodiment of the present invention illustrated, each passageway 29 is preferably mesially offset by an angle of approximately 8° with respect to the tooth abutting surface 31, which angle, of course, can be changed as required. The distal ends 12 can also be ligated to the lingual sheaths 28 in a manner known to those skilled in the art if desired, for example, to prevent a patient from removing the appliance.

Because the patient has a thumbsucking or similar habit, there is an overjet condition, as illustrated typically by the relative positions of the upper central incisor T2 and the lower central incisor T3 in FIG. 4. When the patient's mouth is closed, the second portions 20 extend through the gap formed by the overjet condition between the upper central incisors T2 and the lower central incisors T3, and the circular loops 24 are located anteriorly (or labially) with respect to the lower incisors T3 and posteriorly (or lingually) with respect to the labial vestibule, as shown in FIG. 4. The circular loops 22 are likewise spaced approximately 1 to 2 mm anteriorly from the lower central incisors when the patient's mouth is closed, and approximately 1 to 2 mm posteriorly from the patient's lower lip and labial vestibule.

Thus, one advantage of the appliance of the present invention, is that it typically does not touch the sensitive gingival tissue nor does it engage the labial vestibule. The first portions 16 extend along the lingual side of the patient's maxillary arch spaced away from the teeth of the arch. Thus, the first portions 16 and second portions 20 likewise typically do not engage any of the teeth of the arch, nor do they engage any of the sensitive tissue within the mouth. Accordingly, the orthodontic appliance of the present invention is particularly advantageous in that it should avoid the discomfort caused by contact with the tissue or teeth in the patient's mouth typically associated with prior art habit correcting devices. Another advantage of the appliance of the present invention is that because the portions of the appliance are located either posteriorly with respect to the upper incisors, or posteriorly with respect to the lower lip and labial vestibule, when the patient smiles, the appliance is typically hidden from view.

When the patient's mouth is opened, because the appliance 10 is inserted within the lingual sheaths 28 carried on the upper first molars T1, the appliance 10 moves upwardly with the maxillary arch so that the two circular loops 22 are located within the space between the upper and lower incisors, T2 and T3, respectively. As a result, the two circular loops 22 at least partially block the opening, thus either preventing insertion of the patient's thumb (or other habit instrument) or preventing complete closure of the mouth to suck the thumb (or other habit instrument) when inserted.

One advantage of the appliance of the present invention is that while the circular loops 22 effectively prevent insertion of the thumb (or other habit instrument), the rounded surfaces of the circular loops do not cut or otherwise injure the finger tissue of the patient upon attempting to insert a finger in the mouth. Another advantage of the appliance of the present invention is that it permits the patient to receive food or otherwise permits the insertion of objects or instruments into the mouth when fully opened, yet prevents the patient from sucking the thumb (or other habit instrument) upon closing the mouth. Although when fully opened the mouth can receive a thumb (or other habit instrument), the mouth cannot be closed to suck the thumb, because the circular loops 22 engage the thumb, and thus prevent the mouth from closing until the thumb is removed.

Another advantage of the appliance of the present invention is that the U-shaped loops 18 can be adjusted with pliers, for example, to adjust the position of the second portions 20 and the circular loops 22 relative to the patient's teeth and sensitive tissue within the mouth. For example, by squeezing the sides of the U-shaped loops 18 closer to one another, the circular loops 22 can be pulled closer to the lower central incisor T3. The position of the circular loops 22 can also be adjusted relative to the tissue of the labial vestibule by similarly adjusting the U-shaped loops 18. The U-shaped loops 18 can also be adjusted to adjust the vertical position of the circular loops 22 and, thus, the degree to which the circular loops 22 block the opening to the mouth when opened. Thus, a further advantage of the appliance of the present invention is that it can easily be adjusted to conform to the morphology of a particular patient's mouth. Accordingly, it is possible to manufacture the appliance of the present invention in several standard sizes. Each standard size can then be adjusted, if necessary, by adjusting the U-shaped loops 18 with a pair of pliers to conform to the morphology of each patient's mouth. The appliance of the present invention thus avoids the added costs of prior art habit correcting appliances requiring custom manufacture for each patient.

Thus, the appliance 10 of the present invention is preferably positioned so that the second portions 20 extend anteriorly over the lower incisors T3, as shown in FIG. 4, and through the gap typically formed by an overjet condition without contacting the incisors T2 or T3. The circular loops 22 in turn extend in an approximately vertical orientation, anteriorly with respect to the lower incisors T3 and posteriorly with respect to the labial vestibule and the lower lip when the mouth is closed, preferably without contacting the gingival tissue of the lower incisors nor the tissue of the labial vestibule or lower lip. The two circular loops 22 thus provide a "fence-type" of blockage inhibiting the insertion of a thumb (or other habit instrument).

Once the overjet condition and/or the thumb sucking or similar habit is corrected, the appliance of the present invention can be removed by simply removing the distal ends 12 from the lingual sheaths 28. If necessary, the appliance can later be inserted again by simply inserting the distal ends 12 back into the lingual sheaths 28. The appliance 10 can likewise easily be removed during treatment to adjust the position or shape of the appliance in response to the corrective treatment, for example. Thus, the appliance of the present invention can be particularly advantageous in comparison to prior art devices which are soldered to molar bands, thus requiring removal of the molar bands to remove the appliance. Although the appliance of the present invention could also be soldered to molar bands, the design of the present invention provides an added measure of flexibility by permitting attachment to lingual sheaths, such as the lingual sheaths 28 described above.

As will be recognized by those skilled in the art, numerous features of the appliance 10 described above in connection with FIGS. 1–4 can be changed without departing from the scope of the appended claims. For example, the distal ends 12 of the appliance do not have to be doubled over, nor do they have to be inserted within lingual sheaths of the type described above. The distal ends 12 could equally take the shape of straight portions of wire inserted through round tubes attached to the molars, or numerous other means known to those skilled in the art for attaching orthodontic appliances to molars. The U-shaped loops 18 could likewise take a different form, for example, circular loops, or the forms of other means for adjusting the position, size and shape of a wire appliance known to those skilled in the art. Similarly, the circular loops 22 could take the shape of numerous other means for blocking the opening to the mouth. Although the circular loops 22 are easy to manufacture, a separate member, for example, could equally be coupled to the wire to provide a means for blocking the opening to the mouth in a manner similar to the circular loops. As will also be recognized by those skilled in the art, the appliance of the present invention can equally be used to prevent the insertion of habit instruments other than a thumb, such as other fingers, or to correct other oral habits, such as nail biting.

I claim:

1. An orthodontic appliance for correcting a habit of inserting a habit instrument within a mouth, comprising:
   a frame member including distal ends for being coupled to appliances supported on maxillary molars, and two elongated first portions, each extending anteriorly from a respective distal end; and
   a guard portion coupled at each end thereof to one of the two first portions and including blocking means spaced between said first two portions to deter insertion of a habit instrument within the mouth, said blocking means depending downwardly from said first portions and inclined to facilitate positioning anteriorly with respect to the lower incisors and posteriorly with respect to the lower lip when the mouth is closed, whereupon opening of the mouth, the appliance is carried upwardly with the maxillary arch and the guard portion is moved to a position at least partially within the opening between the upper and lower incisors to deter insertion of a habit instrument within the mouth.

2. An appliance as defined in claim 1, further comprising means for adjusting the position of the frame member and the guard portion.

3. An appliance as defined in claim 2, wherein the frame member is made of wire and the means for adjusting includes a bendable portion located within each respective first portion for bending the respective first portion to correspondingly adjust the position of the frame member and the guard portion.

4. An appliance as defined in claim 3, wherein each bendable portion defines a substantially U-shaped portion of the respective first portion of the wire frame member.

5. An appliance as defined in claim 1, further comprising a pair of lingual sheaths, each being carried on a respective maxillary molar for receiving a respective distal end of the frame member.

6. An appliance as defined in claim 1, wherein the frame member is made of wire and each distal end is doubled over for insertion within an orthodontic appliance carried on a maxillary molar.

7. An appliance as defined in claim 1, wherein the habit instrument is at least one finger.

8. An appliance as defined in claim 1, further comprising two second portions, each extending anteriorly from a respective first portion between the respective first portion and the guard portion, each second portion being curved to extend between a gap formed between the upper and lower incisors upon closure of the mouth.

9. An appliance as defined in claim 8, wherein the first portions, second portions and the guard portion are located to substantially avoid contact with the teeth and gingival and labial tissue upon closure of the mouth.

10. An appliance as defined in claim 5, wherein each lingual sheath defines an opening for receiving a distal end of the frame member which is mesially offset relative to a tooth-abutting surface of the lingual sheath to facilitate removal and insertion of the distal end of the frame member.

11. An orthodontic appliance for deterring insertion of a habit instrument within a mouth, comprising:
two distal ends for being coupled to orthodontic appliances carried on maxillary molars; and
at least one substantially rigid blocking member coupled at each end to the distal ends and spaced therebetween for deterring insertion of a habit instrument within the mouth, said blocking member depending downwardly from said distal ends and inclined to facilitate being located labially with respect to the lower incisors and lingually with respect to the lower lip when the mouth is closed whereupon the appliance is carried upwardly by the maxillary arch upon opening of the mouth and carried downwardly by the maxillary arch upon subsequent closure of the mouth.

12. An orthodontic appliance as defined in claim 11, further comprising:
two first portions, each extending anteriorly with respect to a respective distal end and spaced lingually with respect to the teeth of the maxillary arch.

13. An orthodontic appliance as defined in claim 12, further comprising:
two second portions, each being coupled between a respective first portion and the blocking member, and extending downwardly through a space defined between the upper and lower incisors caused by an overjet condition upon closure of the mouth.

14. An orthodontic appliance as defined in claim 12, further comprising means for adjusting the position of the appliance relative to the teeth and the sensitive tissue within the mouth.

15. An orthodontic appliance as defined in claim 14, wherein the appliance and the first portions are formed of wire, and the means for adjusting includes a bendable portion defined within each respective first portion for bending the respective first portion to correspondingly adjust the position of the appliance.

16. An orthodontic appliance as defined in claim 11, further comprising a pair of lingual sheaths, each being carried on a respective maxillary molar for receiving a respective distal end to carry the appliance on the maxillary molars.

17. An orthodontic appliance as defined in claim 11, wherein the distal ends and the blocking member are formed of wire, and each distal end is doubled over for insertion within an orthodontic appliance carried on a maxillary molar, and the blocking member is formed by at least one loop of the wire.

18. An orthodontic appliance as defined in claim 11, wherein the appliance extends through a space defined between the lower and upper incisors caused by an overjet condition and the blocking member is spaced buccally with respect to the lower incisors and lingually with respect to the lower lip and labial vestibule to substantially avoid contact with the teeth and tissue within the mouth upon closure of the mouth.

19. An orthodontic appliance for correcting a habit of inserting a habit instrument within a mouth, comprising:
a wire member defining distal ends for being coupled to appliances carried on maxillary molars, and two curved portions extending anteriorly with respect to the distal ends through a space between the upper and lower incisors; and
a guard portion coupled at each end thereof to one of the two curved portions and including blocking means spaced between said two curved portions to deter insertion of a habit instrument within the mouth, said blocking means depending downwardly from said two curved portions and inclined to facilitate location in the mouth anteriorly with respect to the lower incisors for deterring insertion of a habit instrument.

20. An orthodontic appliance as defined in claim 19, further comprising at least one bendable portion formed within the wire member for adjusting the position of the appliance within the mouth.

21. An orthodontic appliance for correcting a habit of inserting a habit instrument within a mouth, comprising:
a frame member including distal ends for being coupled to appliances supported on maxillary molars, and two first portions, each extending anteriorly from a respective distal end; and
a guard portion coupled to the two first portions and being located anteriorly with respect to the lower incisors when the mouth is closed, whereupon opening of the mouth, the appliance is carried upwardly with the maxillary arch and the guard portion is located at least partially within the opening between the upper and lower incisors to deter insertion of a habit instrument within the mouth, wherein the frame member is made of wire and the guard portion is formed by at least one loop of the wire.

22. An orthodontic appliance for correcting a habit of inserting a habit instrument within a mouth, comprising:
a frame member including distal ends for being coupled to appliances supported on maxillary molars, and two first portions, each extending anteriorly from a respective distal end; and
a guard portion coupled to the two first portions and being located anteriorly with respect to the lower incisors when the mouth is closed, whereupon opening of the mouth, the appliance is carried upwardly with the maxillary arch and the guard portion is located at least partially within the opening between the upper and lower incisors to deter insertion of a habit instrument within the mouth, wherein the frame member is made of wire and the guard portion is formed by two loops of the wire spaced apart from each other and coupled by a substantially straight portion of the wire.

23. An orthodontic appliance for correcting a habit of inserting a habit instrument within a mouth, comprising:
a wire member defining distal ends for being coupled to appliances carried on maxillary molars, and two curved portions extending anteriorly with respect to the distal ends through a space between the upper and lower incisors; and
a guard portion coupled to the two curved portions and being located anteriorly with respect to the lower incisors for deterring insertion of a habit instrument, wherein the guard portion is defined by at least one loop of the wire member.

* * * * *